(12) United States Patent
Moskowitz et al.

(10) Patent No.: US 6,951,059 B2
(45) Date of Patent: Oct. 4, 2005

(54) COMPASS-BASED INDICATOR WITH MAGNETIC SHIELDING

(75) Inventors: Ari Moskowitz, Santa Barbara, CA (US); Marc Stepkowski, Ventura, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/042,400

(22) Filed: Jan. 25, 2005

(65) Prior Publication Data

US 2005/0120571 A1    Jun. 9, 2005

Related U.S. Application Data

(63) Continuation of application No. 10/631,904, filed on Jul. 31, 2003, now Pat. No. 6,883,241.

(51) Int. Cl.[7] .................. G01C 17/02; A61M 5/48
(52) U.S. Cl. .................. 33/355 R; 33/354; 604/9
(58) Field of Search .................. 33/354–358, 613, 33/645; 128/899; 604/8, 9, 19, 500

(56) References Cited

U.S. PATENT DOCUMENTS

| | | | | |
|---|---|---|---|---|
| 3,875,676 A | * | 4/1975 | Hamilton | 33/345 |
| 3,902,252 A | * | 9/1975 | Farber | 33/356 |
| 4,109,391 A | * | 8/1978 | Wing | 33/354 |
| 4,625,573 A | * | 12/1986 | Henry | 324/377 |
| 5,602,472 A | * | 2/1997 | Bergstedt et al. | 324/207.25 |
| 5,643,194 A | * | 7/1997 | Negre | 604/8 |
| 5,709,225 A | * | 1/1998 | Budgifvars et al. | 128/899 |
| 6,670,874 B1 | * | 12/2003 | Galli | 335/205 |
| 6,736,222 B2 | * | 5/2004 | Kuckes et al. | 175/45 |
| 2002/0022793 A1 | * | 2/2002 | Bertrand et al. | 604/9 |
| 2002/0058901 A1 | * | 5/2002 | Marion | 604/9 |
| 2002/0108623 A1 | * | 8/2002 | Rehder et al. | 128/899 |
| 2003/0032915 A1 | * | 2/2003 | Saul | 604/9 |
| 2004/0019272 A1 | * | 1/2004 | Witcraft | 600/410 |
| 2004/0260229 A1 | * | 12/2004 | Meir | 604/9 |
| 2005/0004460 A1 | * | 1/2005 | Taylor et al. | 600/437 |

* cited by examiner

Primary Examiner—G. Bradley Bennett
(74) Attorney, Agent, or Firm—Shumaker & Sieffert, PA

(57) ABSTRACT

The invention is directed toward a magnetic shield included in a compass-based indicator tool. The indicator tool utilizes a compass to indicate a device setting of an implantable medical device. The implantable medical device may include a target that creates an internal magnetic field for the compass to interact with. External magnetic fields, specifically earth's magnetic field, may interfere with the compass and create an incorrect device setting indication. The magnetic shield blocks the external magnetic fields from influencing the accuracy of the device setting measurement.

3 Claims, 11 Drawing Sheets

COMPASS-BASED INDICATOR WITH MAGNETIC SHIELDING

This is a continuation of U.S. patent application Ser. No. 10/631,904, now U.S. Pat. No. 6,883,241 filed Jul. 31, 2003, the entire content of which is incorporated herein by reference.

FIELD OF THE INVENTION

The invention relates to medical devices and, more particularly, to compass-based indicator tools.

BACKGROUND

Compass-based indicator tools are used to determine a setting of an implantable medical device. The implantable medical device may include a fluid flow control valve that controls the pressure of cerebral spinal fluid (CSF) in a patient's brain. Excessive accumulation of cerebral spinal fluid (CSF), due to hydrocephalus or other causes, manifests itself as increased pressure within the brain. Relieving the CSF pressure is therapeutically beneficial and is usually done by using a fluid flow control valve to drain CSF from ventricles in the brain.

The implantable medical device may include a target in the form of a magnet. The magnet allows a tool set to determine the setting of the medical device and change the setting without removing the subcutaneously implanted device. The tool set typically includes a locator tool to determine the orientation of the medical device, the compass-based indicator tool to determine the setting of the implantable medical device by using a compass, and an adjustment tool to change the setting of the medical device by using another magnet. The tool set works by using magnetic coupling between the magnet on the implantable medical device and the indicator tool compass and the adjustment tool magnet.

The indicator tool relies on an interaction between the magnet on the medical device and the compass that is strong enough to determine the position of the magnet even through a patient's scalp. The magnet-compass interaction must also be resistant to external magnetic fields, especially from the earth. The compass will drift toward aligning with the earth's magnetic field if the pull of the magnet in the implanted medical device is not strong enough. The deflection angle increases as the distance between the magnet and the compass increases, and may lead to inaccurate device setting indications.

U.S. Published Patent Application No. 2002/0022793 to Bertrand et al. discloses a compass-based indicator for assessing the position of a fluid flow valve within an implanted device. The fluid flow valve described by Bertrand et al. may be used for controlling the flow of cerebral spinal fluid (CSF) in a patient with hydrocephalus. U.S. Published Patent Application No. 2003/0032915 to Saul discloses an implantable valve system for controlling the flow of CSF. U.S. Published Patent Application No. 2003/0058901 to Marion describes another implantable valve system for controlling the flow of CSF. Table 1 below lists documents that disclose devices for controlling flow of CSF.

TABLE 1

| Pat. No. | Inventors | Title |
| --- | --- | --- |
| 2002/0022793 | Bertrand et al. | Tool for adjusting an implantable adjustable fluid flow control valve |
| 2003/0032915 | Saul | System and method for treating elevated intracranial pressure |
| 2002/0058901 | Marion | Implantable subcutaneous value for the treatment of hydrocephalus, and adjusting devices therefor |

All documents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the structures and techniques of the present invention.

SUMMARY

In general, the invention is directed to a magnetic shield included in a compass-based indicator tool for interaction with an implanted medical device to assess a setting associated with the device. The invention has certain objects. That is, various embodiments of the present invention provide solutions to one or more problems existing in the prior art with respect to the compass-based indicator tools for interaction with implanted medical devices.

The problems include, for example, inaccuracies in the setting indication provided by a compass-based indicator tool due to the effects of external magnetic fields. The compass-based indicator tool interacts with a magnetic target that creates an internal magnetic field, and causes the compass to indicate a particular position. The position of the compass is indicative of the setting of the implantable medical device, e.g., the position of a fluid flow valve. External magnetic fields, and especially the earth's magnetic field, may interfere with the compass and create an incorrect device setting indication.

Various embodiments of the present invention have the object of solving the foregoing problems. For example, it is an object of the present invention to overcome at least some of the disadvantages of the foregoing procedures by providing a compass-based indicator tool that produces more accurate and reliable indications of implantable device settings. To that end, it is a further object of the present invention to reduce the effects of an external magnetic field on the compass-based indicator tool, and thereby enhance the accuracy of the tool. It is another object of the invention to reduce the effects of an external magnetic field with a shield structure that is relatively unobtrusive and does not interfere with use of the compass-based indicator tool.

Various embodiments of the invention may possess one or more features capable of fulfilling the above objects. In general, the invention is directed to a compass-based indicator tool that includes a magnetic shield. The magnetic shield blocks at least a portion of the external magnetic fields from influencing the accuracy of the device setting measurement. In addition, the magnetic shield can be configured with a relatively low profile to avoid interference with use of the compass-based indicator tool.

In one embodiment, the invention is directed to a compass-based indicator tool comprising a housing, a compass disposed within the housing, and a magnetic shield surrounding at least a portion of the compass.

In another embodiment, the invention is directed to a locator tool comprising a housing, a compass-based indicator tool received by the housing, and a magnetic shield surrounding at least a portion of the compass-based indicator tool.

In another embodiment, the invention is directed to a system comprising an implantable medical device that includes a first magnet to indicate a current device setting, a locator tool to locate the implantable medical device within a patient, and an adjustment tool that includes a second magnet that interacts with the first magnet to change the current device setting. The system also includes an indicator tool comprising a compass that interacts with the first magnet to determine the current device setting, and a magnetic shield surrounding at least a portion of the compass to reduce effects of a magnetic field on the compass.

In another embodiment, the invention is directed to a method which comprises mounting a compass-based indicator tool adjacent to an implantable medical device, shielding a compass disposed within the compass-based indicator tool from magnetic fields, and indicating a device setting of the implantable medical device, wherein the device setting is indicated by the compass.

In comparison to known implementations of compass-based indicator tools for implantable medical devices, various embodiments of the present invention may provide one or more advantages. For example, if the implantable medical device is implanted subcutaneously on a patient's skull, a compass-based indicator tool in accordance with the invention is capable of taking a more accurate device setting measurement through the patient's skin. As the compass-based indicator tool moves further away from the implantable medical device, the external magnetic fields have a greater influence on the compass. The magnetic shield blocks the external magnetic fields from corrupting the device setting measurement, even as the distance between the indicator tool and the implantable medical device increases. The compass is then able to indicate accurate device setting values in the cases where the patient's skin is thicker than normal. In this way, the magnetic shield may eliminate the need for x-rays to determine an implantable medical device setting through a surface, such as a patient's skin.

In addition, the magnetic shield may be substantially unobtrusive and generally invisible to a user of the compass-based indicator tool. The effect of external magnetic fields on the device setting measurements may be significantly reduced even if the magnetic shield is small. For example, if the magnetic shield is disposed in a recess of the compass-based indicator tool housing, the magnetic shield may be generally hidden from the user's view. This recess may be shallow, but if the magnetic shield is able to substantially surround the compass, the external magnetic fields have a lesser influence on the device setting measurement.

It is a primary object of the present invention to provide an improvement to fastening compass-based indicator tools for use with implantable medical devices. This and other objects of the invention will become clear from an inspection of the detailed description of the invention and from the appended claims. Throughout the description, like elements are referred to by like reference numbers. An element referred to by a reference number has all the attributes and characteristics of the element as described wherever in the description unless specifically stated otherwise.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

Figure 1:
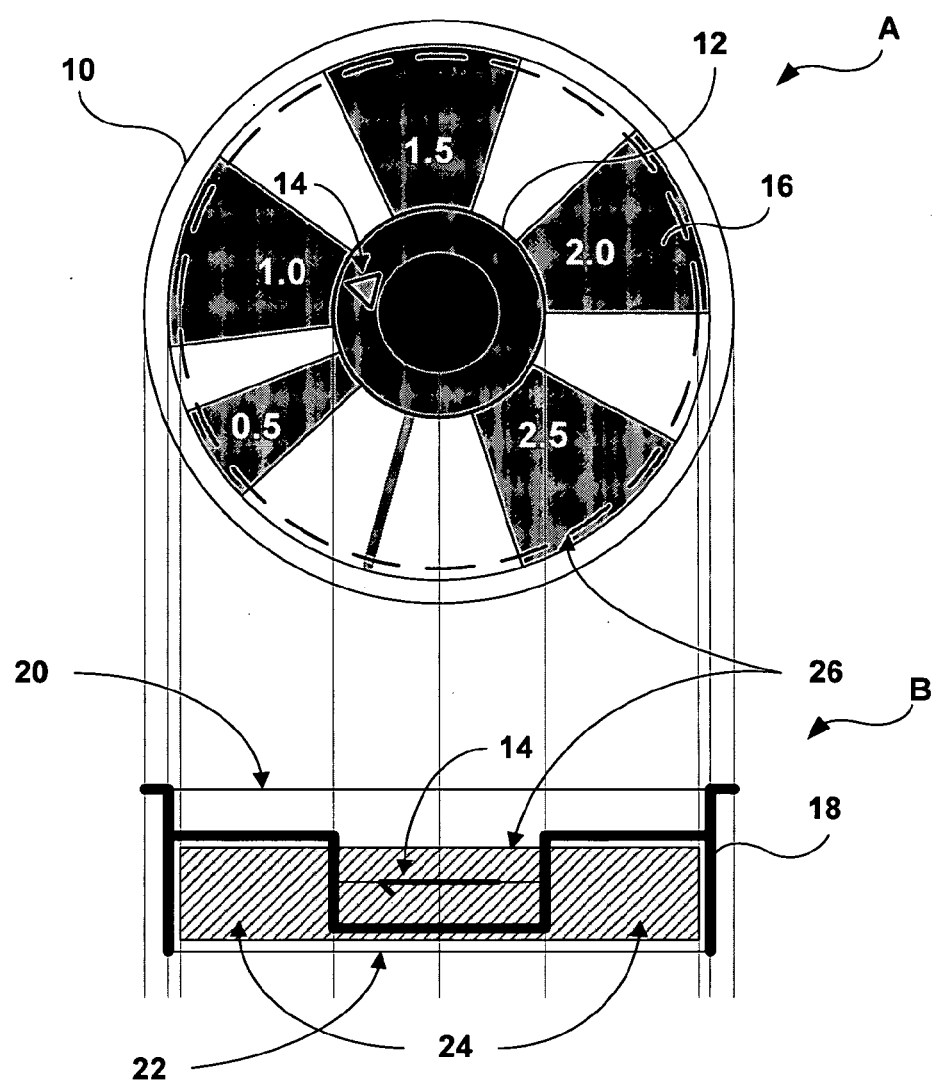
FIG. 1 is a schematic diagram illustrating a compass-based indicator tool according to an embodiment of the invention.

FIG. 1 is a schematic diagram illustrating a compass-based indicator tool 10 according to an embodiment of the invention. Indicator tool 10 includes a compass 12, a compass needle 14, a device setting index 16, a housing 18, and a magnetic shield 26. Housing 18 may include an indicating side 20, a sensing side 22, and an annular recess 24 located on the sensing side 22 between the outer rim of indicator tool 10 and the outer diameter of the compass 12. In this case, magnetic shield 26 has an annular shape and is inserted into recess 24, which completely surrounds compass 12. For purposes of illustration, FIG. 1 includes both a plan view A of indicating side 20 and a cross-sectional side view B of indicator tool 10. Side view B shows the structure of housing 18 and magnetic shield 26 disposed within recess 24.

Indicator tool 10 may be used to determine an implantable device setting. The implantable device (not shown) includes a target that is positioned according to the device setting. The target creates a localized magnetic field around the implantable device with a direction relative to the device setting. Compass needle 14 interacts with the localized magnetic field when sensing side 22 of indicator tool 10 is placed adjacent to the implantable device. Compass needle 14 indicates the device setting by pointing to a region on device setting index 16 located on indicating side 20. Device setting index 16 is designed to properly align with the location of the target for each device setting value. For example, housing 18 may be mounted on a locator tool that conforms to the profile of a subcutaneously implanted device to align indicator tool 10 in the proper orientation relative to the implanted device. In FIG. 1, device setting index 16 comprises a numerical scale from 0.5 to 2.5.

Compass 12 may be affected by an external magnetic field, especially the magnetic field of the earth. Compass needle 14 may deflect toward the orientation of the external magnetic field, and the deflection angle may increase as compass-based indicator tool 10 moves further away from the device. The influence of the external magnetic field may cause compass pointer 14 to indicate an incorrect device setting value, particularly when the target is further away from compass 12. For example, for patients with thicker skin, the implanted device may reside at a greater depth below the skin surface. In order to improve the accuracy of indicator tool 10, magnetic shield 26 is placed around compass 12. Magnetic shield 26 may extend above and below compass needle 14.

As indicator tool 10 moves away from the device, the interaction between compass 12 and the internal magnetic field of the device target becomes weaker. The external magnetic fields may then have a greater influence on compass needle 14. Magnetic shield 26 serves to shield compass 12 from the external magnetic field to allow accurate device setting measurements even when indicator tool 10 and the device are separated by a greater distance.

Magnetic shield 26 may be made out of a material that cannot be substantially penetrated by magnetic fields. The material may have high permeability, low saturation, and attenuation properties sufficient to reduce the effects of the external magnetic field on compass 12. As one example, a suitable magnetic shielding material is commercially available from Amuneal Manufacturing Corporation, of Philadelphia, Pa., under the tradename "Amumetal." Amumetal is a hydrogen annealed 80% Nickel-Iron Alloy that has a maximum permeability of approximately 400,000H/m and a density of approximately 8.747 g/cm$^3$. Amumetal is available in 3 meter long sheets with a variety of thicknesses, ranging from an approximately 0.102 mm thick foil to an approximately 3.175 mm thick sheet, and a variety of widths, including approximately 0.76 m, 0.61 m, and 0.41 m and smaller. Other magnetic shielding materials may be used, however, provided they provide reasonable shielding against external magnetic forces.

Magnetic shield 26 may be configured in several different ways including wrapping layers of the material around a ring-like frame in concentric passes, stacking annular disks of the material vertically adjacent to one another, wrapping a sheet of the material into a cylindrical shape, or the like. The listed configurations of magnetic shield 26 may be optimized to a thickness; height, and radius to effectively block at least a portion of external magnetic fields and to fit into recess 24. According to one specific example, recess 24 may be approximately 17.8 mm wide, approximately 10.2 mm deep, and have an outer radius of approximately 27.9 mm. Any of the configurations of magnetic shield 26 may then be inserted into recess 24. Magnetic shield 26 may be held in recess 24 by friction fitting, adhesive bonding, potting in epoxy, welding or the like. The foregoing techniques may also make magnetic shield 26 substantially unobtrusive and virtually invisible to a user of compass-based indicator tool 10.

In one embodiment, the implanted device may be an adjustable fluid flow control valve controlling the flow of cerebral spinal fluid (CSF) in a patient with hydrocephalus. The valve is implanted subcutaneously on the patient's skull to drain away excess CSF and maintain normal CSF pressure in the brain. The adjustable valve includes a magnet embedded in a base. The fluid pressure is changed by rotating the base, which also moves the magnet, to open and close the valve to thereby adjust the valve setting. When coupled to the magnet, compass needle 14 changes direction with a change in the fluid pressure setting, and indicates the value by its location on device setting index 16. With the addition of magnetic shield 26, precise valve readings may be taken through the patient's skin even when the scalp is thicker than normal, which forces indicator tool 10 to be further away from the adjustable valve. In particular, magnetic shield 26 reduces the effects of external magnetic fields on compass 12, allowing more precise interaction between compass needle 14 and the magnet carried by the implantable device. In this way, indicator tool 10 may eliminate the need for x-rays to determine the valve setting, potentially reducing x-ray exposure for the patient.

Figure 2:
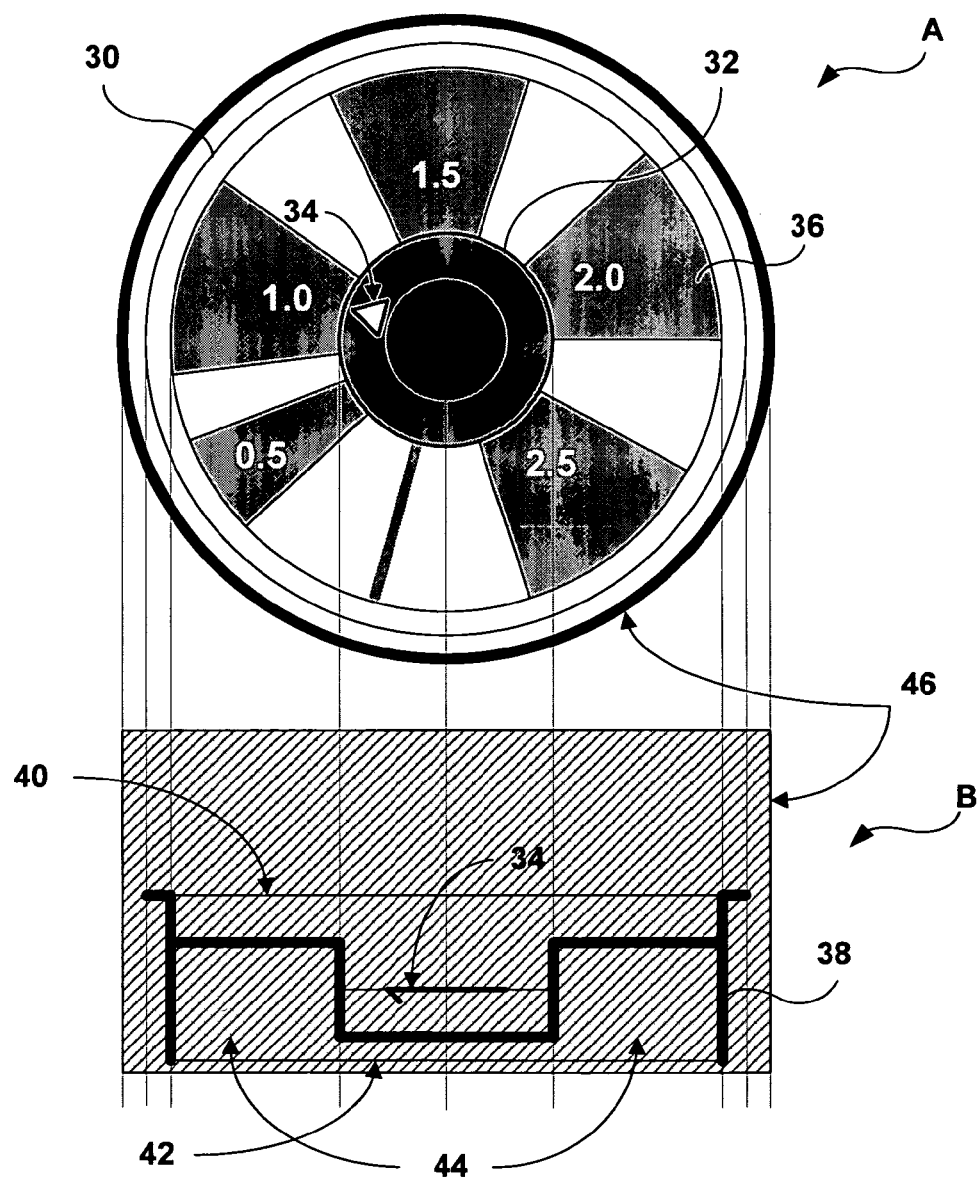
FIG. 2 is a schematic diagram illustrating another compass-based indicator tool.

FIG. 2 is a schematic diagram illustrating another compass-based indicator tool 30. Indicator tool 30 substantially conforms to indicator tool 10 of FIG. 1, but includes an external magnetic shield 46. External magnetic shield 46 may have an increased height in some embodiments. As shown in FIG. 2, indicator tool 30 includes a compass 32, a compass needle 34, a device setting index 36, a housing 38, and a magnetic shield 46. Housing 38 may include an indicating side 40, a sensing side 42, and a recess 44 located on the sensing side 42 between the outer rim of indicator tool 30 and the outer diameter of the compass 32. In this case, magnetic shield 46 has an annular shape and forms a cylinder that is slid over the outer wall of housing 38. Magnetic shield 46 may extend both above and below compass needle 34 and may cover all of housing 38 of indicator tool 30. A plan view A of indicating side 40 and a cross-sectional side view B of indicator tool 30 are shown in FIG. 2. Side view B shows the structure of housing 38 and magnetic shield 46 surrounding indicator tool 30.

When the sensing side 42 of indicator tool 30 is placed adjacent to an implantable device, compass needle 34 interacts with a magnetic target included in the implantable device. Compass needle 34 then aligns in the direction of the localized magnetic field generated by the device target, and indicates an implantable device setting value by pointing to a region on device setting index 36 located on the indicating side 40. Device setting index 36 is aligned with the location of the target at specific implantable device setting values.

Magnetic shield 46 at least partially blocks an external magnetic field, such as the earth's magnetic field, from influencing compass 32. Without magnetic shield 46, compass needle 34 may align with the external magnetic field instead of the localized magnetic field created by the device target. The effect of the external magnetic field on compass 32 may increase as indicator tool 30 is moved away from the device. By blocking at least a portion of the external magnetic field, an accurate reading may be taken, even if the device and indicator tool 30 are separated.

Magnetic shield 46 may be made out of a material that can withstand the effects of magnetic fields as described in reference to magnetic shield 26 of FIG. 1. As in the example of FIG. 1, magnetic shield 46 is selected to have a certain thickness, height, and radius to effectively block external magnetic fields and fully wrap around housing 38, which, in one specific example, may be approximately 15.3 mm tall and have a radius of approximately 35.5 mm. Magnetic shield 46 may then be slid over indicator tool 30 prior to taking the device setting measurement. In the example of FIG. 2, magnetic shield 46 need not be attached to indicator tool 30, and may be removable by the user. In other embodiments, magnetic shield 46 can be attached to housing 38 of indicator tool 30, if desired, e.g., by friction fitting, adhesive bonding, ultrasonic welding or the like. Magnetic shield 46 may be formed from materials as described above with reference to FIG. 1.

Figure 3:
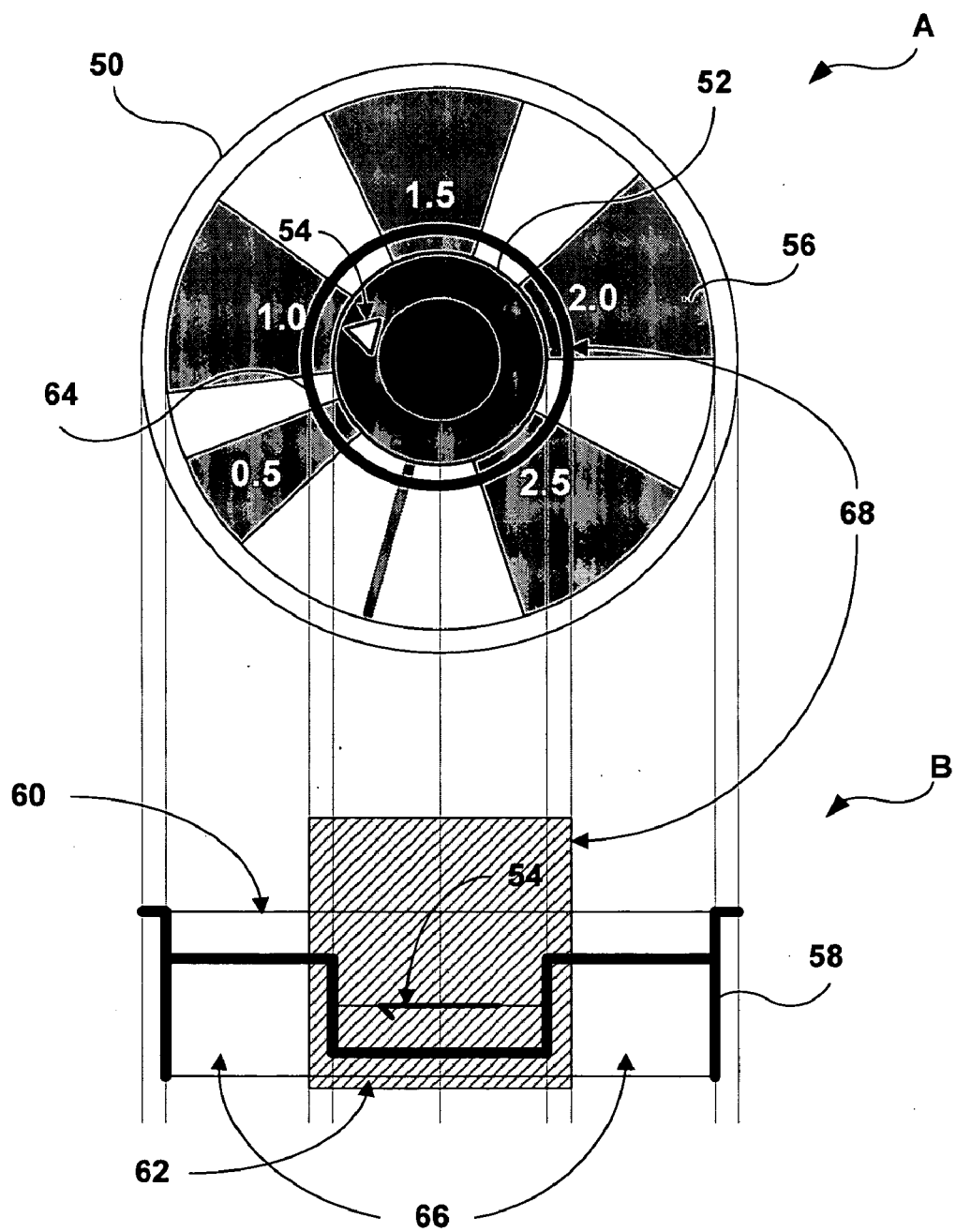
FIG. 3 is a schematic diagram illustrating another compass-based indicator tool.

FIG. 3 is a schematic diagram illustrating another compass-based indicator tool 50. Indicator tool 50 includes a compass 52, a compass needle 54, a device setting index 56, a housing 58, and a magnetic shield 68. Housing 58 may include an indicating side 60, a sensing side 62, an annular groove 64, and a recess 66 located on the sensing side 62 between the outer rim of indicator tool 50 and the outer diameter of the compass 52. In this case, magnetic shield 68 has an annular shape and forms a cylinder that is inserted into annular groove 64, which is formed within housing 58 around compass 52. Annular groove 64 may be accessible from at least one of indicating side 60 and sensing side 62. Magnetic shield 68 may be large enough to extend both above and below compass needle 54 and may extend beyond indicating side 60 of housing 58. A plan view A of indicating side 60 and a cross-sectional side view B of indicator tool 50 are shown in FIG. 3. The side view shows the structure of housing 58 and magnetic shield 68 disposed within annular groove 64.

Magnetic shield 68 blocks at least a portion of external magnetic fields from influencing compass 52. Without magnetic shield 68, compass needle 54 may align with an external magnetic field, such as the earth's magnetic field, instead of the localized magnetic field created by a magnet embedded in the implantable device. As indicator tool 50 is moved further away from the implantable device, the effect of the external magnetic field on compass 52 may increase. The addition of magnetic shield 68 allows an accurate reading to be taken, even when the device and indicator tool 50 are separated.

Magnetic shield 68 is formed from a material that conforms to the material properties discussed in reference to magnetic shield 26 of FIG. 1. Magnetic shield 68 may conform to a thickness, height, and radius to optimally reduce the effects of external magnetic fields on compass 52, and to fit into annular groove 64, which, in one specific example, may be approximately 17.8 mm wide, 10.2 mm deep, and have an outer radius of 27.9 mm. Magnetic shield 68 may then be inserted into annular groove 64 and held by friction fitting, adhesive bonding, potting in epoxy, welding or the like. The previous techniques may also make magnetic shield 68 substantially unobtrusive to a user of compass-based indicator tool 50, if magnetic shield 68 does not extend above housing 58.

Figure 4:
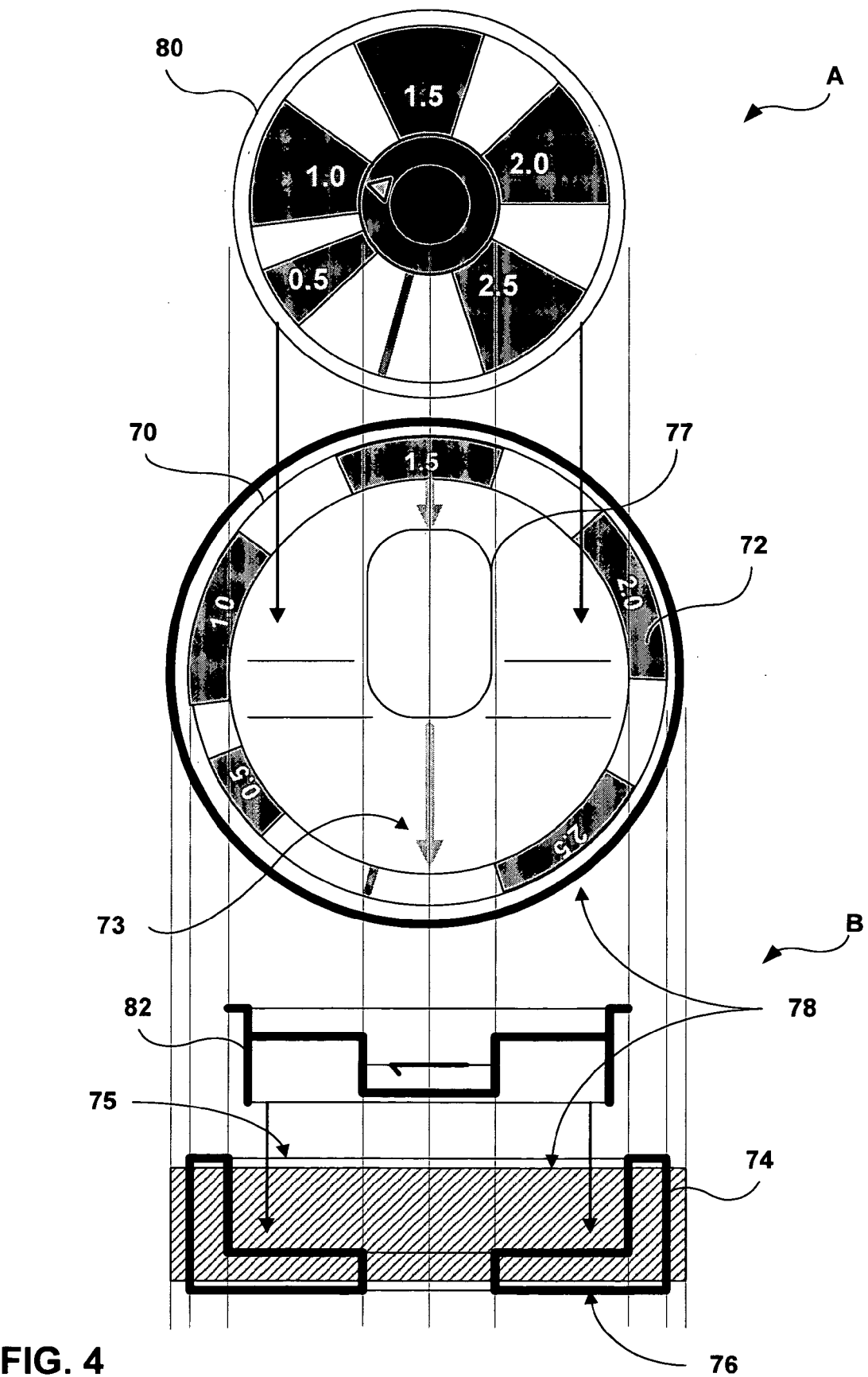
FIG. 4 is a schematic diagram illustrating a locator tool in accordance with an embodiment of the invention.

FIG. 4 is a schematic diagram illustrating a locator tool 70 in accordance with an embodiment of the invention. Locator tool 70 includes a device setting index 72, an orientation arrow 73, a housing 74, and a magnetic shield 78. Housing 74 may include a receiving side 75, a locating side 76, and an opening 77 located on locating side 76. In this case, magnetic shield 78 has an annular shape and is slid over housing 74 of locator tool 70. Magnetic shield 78 may cover all of housing 74 of locator tool 70. A plan view A of receiving side 75 and a cross-sectional side view B of locator tool 70 are shown in FIG. 4. Side view B shows the structure of housing 74 and magnetic shield 78 surrounding locator tool 70. FIG. 4 also illustrates a compass-based indicator tool 80 coupling to locator tool 70. Side view B shows an indicator tool housing 82 coupling to locator tool housing 74.

Indicator tool 80 may correspond to any of indicator tools 10, 30, or 50. Indicator tool 80 is received by receiving side 75 of locator tool 70. Indicator tool 80 may be properly oriented by aligning with the device setting index 72. Indicator tool housing 82 may further mate with housing 74 through conformal shapes disposed on indicator tool housing 82 and on housing 74 (not shown), or by some other means used to couple tools 70 and 80 to one another.

Locator tool 70 may be used to specify the orientation of an implantable device. Opening 77 may be designed to fit over the implantable device in only one direction. When fit properly, orientation arrow 73 points in the orientation direction of the device. In one embodiment, the device is a fluid flow control valve implanted subcutaneously on a patient's skull. Locator tool 70 is oriented to the valve by palpating the valve through the patient's skin. The subcutaneous profile of the valve is then fit into opening 77. Indicator tool 80 may couple to locator tool 70 and be correctly oriented with respect to the valve. Indicator tool 80, coupled to locator tool 70, may also include a magnetic shield (not shown). The additional magnetic shield along with magnetic shield 78 may increase overall shield performance and improve the device setting measurement taken by indicator tool 80.

Again, magnetic shield 78 may be made out of a material that can withstand the effects of magnetic fields as discussed in reference to magnetic shield 26 of FIG. 1. Magnetic shield 78 may conform to a thickness, height, and radius to effectively block out at least a portion of the external magnetic fields and fully wrap around housing 74, which, in one specific example, may be approximately 16.3 mm tall, and have a radius of approximately 42.5 mm. Magnetic shield 78 may then be slid over locator tool 70 prior to taking the device setting measurement with indicator tool 80. In the example of FIG. 4, magnetic shield 78 need not be attached to locator tool 70, and may be removable by the user. In other embodiments, magnetic shield 78 can be attached to housing 74 of locator tool 70, if desired, e.g., by friction fitting, adhesive bonding, ultrasonic welding, or the like.

Figure 5:
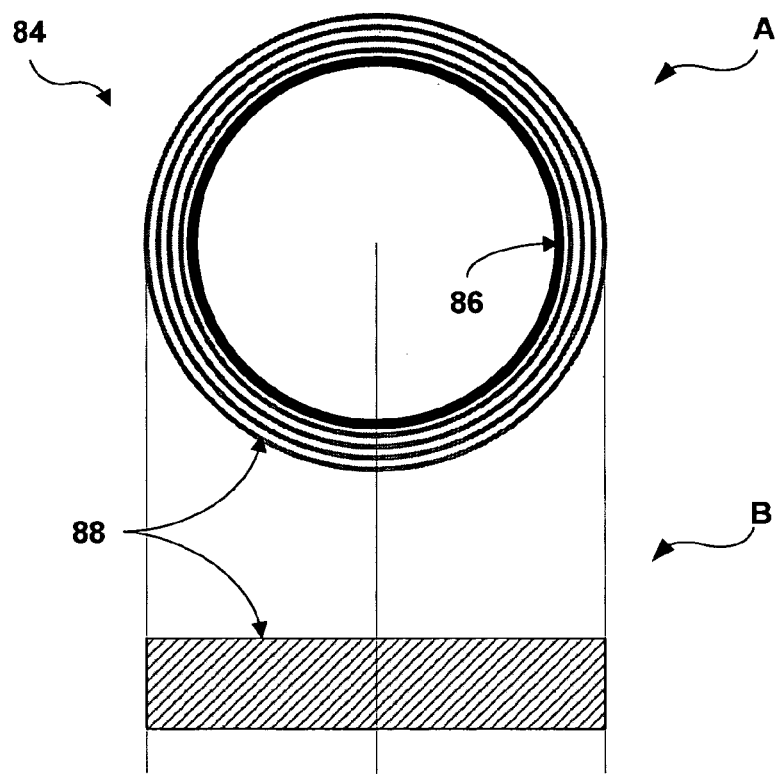
FIG. 5 is a schematic diagram illustrating an exemplary embodiment of a magnetic shield included in a compass-based indicator tool or a locator tool.

FIG. 5 is a schematic diagram illustrating an exemplary embodiment of a magnetic shield 84 included in a compass-based indicator tool conforming to any of indicator tools 10, 30, or 50 or a locator tool conforming to locator tool 70. Magnetic shield 84 includes a ring-like frame 86 and layers of a material 88 that are concentrically wrapped around ring-like frame 86. A plan view A and a cross-section side view B are shown in FIG. 5.

Magnetic shield 84 may be used to block external magnetic fields, such as the earth's magnetic field, from influencing a compass disposed within the indicator tool. Ring-like frame 86 may be made out of plastic or other dielectric materials to avoid interfering with the compass during a device setting measurement. The layers of the material 88 are made from a material substantially similar to the material described in reference to magnetic shield 26 of FIG. 1.

Magnetic shield 84 may be formed in several different ways. For example, the layers of the material 88 may comprise multiple strips of magnetic shielding foil, wrapped about ring-like frame 86. As one specific example, the layers of the material 88 may include nine, 7 mm wide and 304.8 mm long strips cut from the 0.102 mm thick Amumetal foil. Each strip is wrapped concentrically around ring-like frame 86. This configuration results in an overall shield thickness of 5 mm. As the Amumetal foil is continually wrapped around ring-like frame 86, the shielding performance of magnetic shield 84 improves. The layers of material 88 may include a layer of dielectric adhesive between adjacent layers to hold the layers together and to further increase the shielding performance.

In one embodiment, magnetic shield 84 is disposed in a recess located on a sensing side of the compass-based indicator tool, as described in reference to FIG. 1. The recess, in one specific example, may be approximately 17.8 mm wide, 10.2 mm deep, and have an outer radius of 27.9 mm. Magnetic shield 84 conforms to these dimensions in order to fit within the recess. Ring-like frame 86 may have a radius slightly smaller than the outer radius of the recess. Magnetic shield 84 may be friction fit, potted in epoxy, adhesively bonded, or the like to be secured in the recess and be unobtrusive and invisible to a user of the compass-based indicator tool. In other embodiments, magnetic shield 84 may have a different thickness, height, or radius to fit into a groove formed around the compass in the compass-based indicator tool housing, to fit around the entire indicator tool housing or the locator tool housing, or the like to block external magnetic fields from interfering with the device setting measurement.

Figure 6:
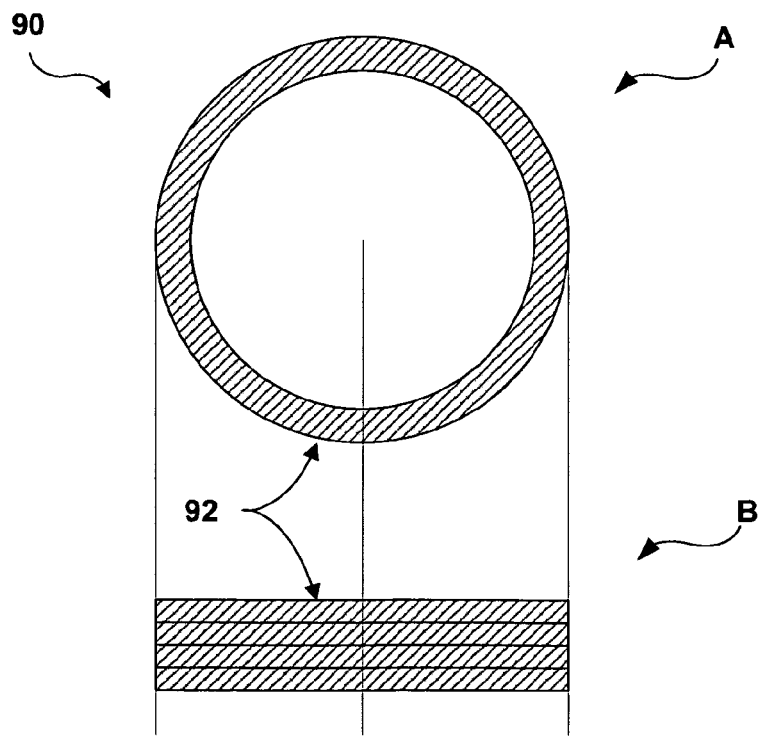
FIG. 6 is a schematic diagram illustrating another exemplary embodiment of a magnetic shield included in a compass-based indicator tool or a locator tool.

FIG. 6 is a schematic diagram illustrating another exemplary embodiment of a magnetic shield 90 included in a compass-based indicator tool conforming to any of indicator tools 10, 30, or 50 or a locator tool conforming to locator tool 70. Magnetic shield 90 includes an annular disk 92. Magnetic shield 90 may conform to a single annular disk 92 or a plurality of annular disks 92 stacked vertically adjacent to one another. A plan view A and a cross-sectional side view B are shown in FIG. 6; side view B illustrates the stack of annular disks 92.

Magnetic shield 90 may be used in an indicator tool including a compass to block external magnetic fields from influencing a device setting measurement. Annular disk 92 is formed from a material conforming to the properties discussed in reference to magnetic shield 26 of FIG. 1. The vertical stack of annular disks 92 forms a substantially annular wall. Each single annular disk 92 may be formed out of a thicker piece of Amumetal plate or a thin piece of Amumetal foil. In either case, stacking several annular disks 92 will improve the performance of magnetic shield 90. The stack of metal foil annular disks 92 may include a dielectric adhesive between each layer to hold the layers together and to further increase the shielding performance.

In one embodiment, magnetic shield 90 is disposed in a recess located on a sensing side of the compass-based indicator tool, as described in reference to FIG. 1. Annular disk 92 conforms to a thickness and radius to match the recess, which, in one specific example, may be approximately 17.8 mm wide and have an outer radius of approximately 27.9 mm. In one embodiment, the stack of annular disks 92 that make up magnetic shield 90 conforms to a height of 10.2 mm in order to fit within the recess. Magnetic shield 90 may be friction fit, potted in epoxy, adhesively bonded, or the like to be secured in the recess and be unobtrusive to a user of the compass-based indicator tool. In other embodiments, magnetic shield 90 may have a different thickness, height, or radius to fit into a groove formed in the compass-based indicator tool housing around the compass, to fit around the entire indicator tool housing or the locator tool housing, or the like to block external magnetic fields from the compass.

Figure 7:
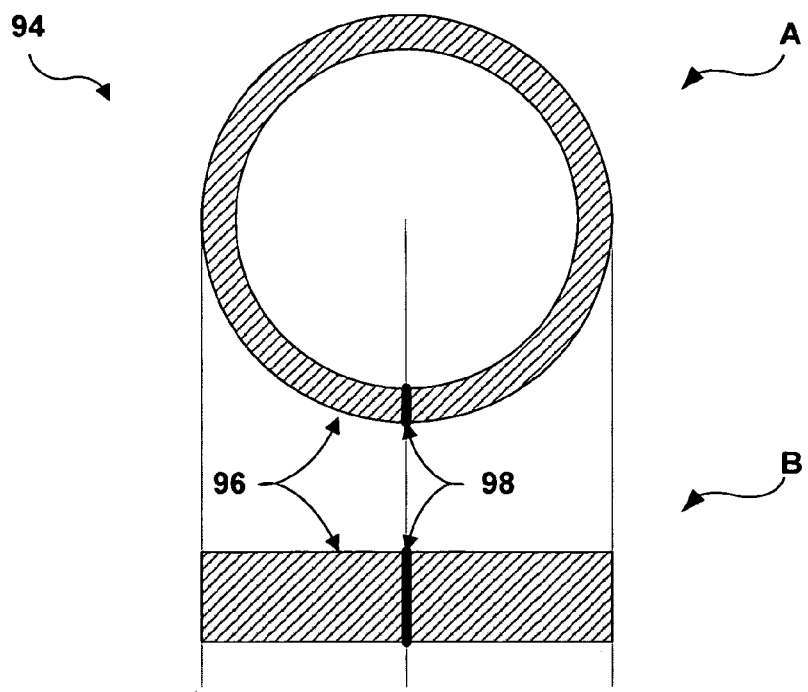
FIG. 7 is a schematic diagram illustrating another exemplary embodiment of a magnetic shield included in a compass-based indicator tool or a locator tool.

FIG. 7 is a schematic diagram illustrating another exemplary embodiment of a magnetic shield 94 included in a compass-based indicator tool conforming to any of indicator tools 10, 30, or 50 or a locator tool conforming to locator tool 70. Magnetic shield 94 includes a substantially cylindrical element 96 formed by bending or wrapping a rectangular piece of material, and a seam 98 where the opposite ends of the material meet to form cylindrical element 96. A plan view A and a cross-section side view B are shown in FIG. 7.

Magnetic shield 94 may be used in an indicator tool to block external magnetic fields from influencing a compass during a device setting measurement. Cylindrical element 96 is made from a material substantially similar to the material discussed in reference to FIG. 1. Magnetic shield 94 is formed by wrapping a rectangular sheet of the material into substantially cylindrical element 96. The opposite ends of the material meet to create seam 98; seam 98 may be sealed or left open. Cylindrical element 96 may be formed from a thicker piece of Amumetal plate or a thin piece of Amumetal foil. In either case, the material can be layered to increase the performance of magnetic shield 94. A dielectric adhesive may be used to hold any layers together and to further increase the shielding performance.

In one embodiment, magnetic shield 94 is disposed within a groove formed in a compass-based indicator tool housing, as described in reference to FIG. 3. In this case, the groove is annular and formed into the housing around the compass. The groove may be accessible by at least one of an indicating side or a sensing side of the housing. As one specific example, cylindrical element 96 has a height of approximately 76.2 mm and radius of approximately 22.2 mm to match the size of the annular groove which may have an inner radius of approximately 19 mm and an outer radius of approximately 27.9 mm. The compass is located at the center of cylindrical element 96. The metal foil is used to make magnetic shield 94, in order to fit into the 17.8 mm wide groove. In this embodiment, magnetic shield 94 may be friction fit, potted in epoxy, adhesively bonded, welded or the like to be secured in the recess. Magnetic shield 94 may be unobtrusive to a user of the compass-based indicator tool if cylindrical element 96 has a height that is smaller than the height of the housing. If the groove is formed through the entire housing, as in FIG. 3, cylindrical element 96 may extend beyond both the sensing side and the indicating side of the housing and will be highly visible to the user.

In other embodiments, magnetic shield 94 may have a different thickness, height, or radius to fit into a recess formed in the compass-based indicator tool housing around the compass, to fit around the entire indicator tool housing or the locator tool housing, or the like to block external magnetic fields from the compass.

Figure 8:
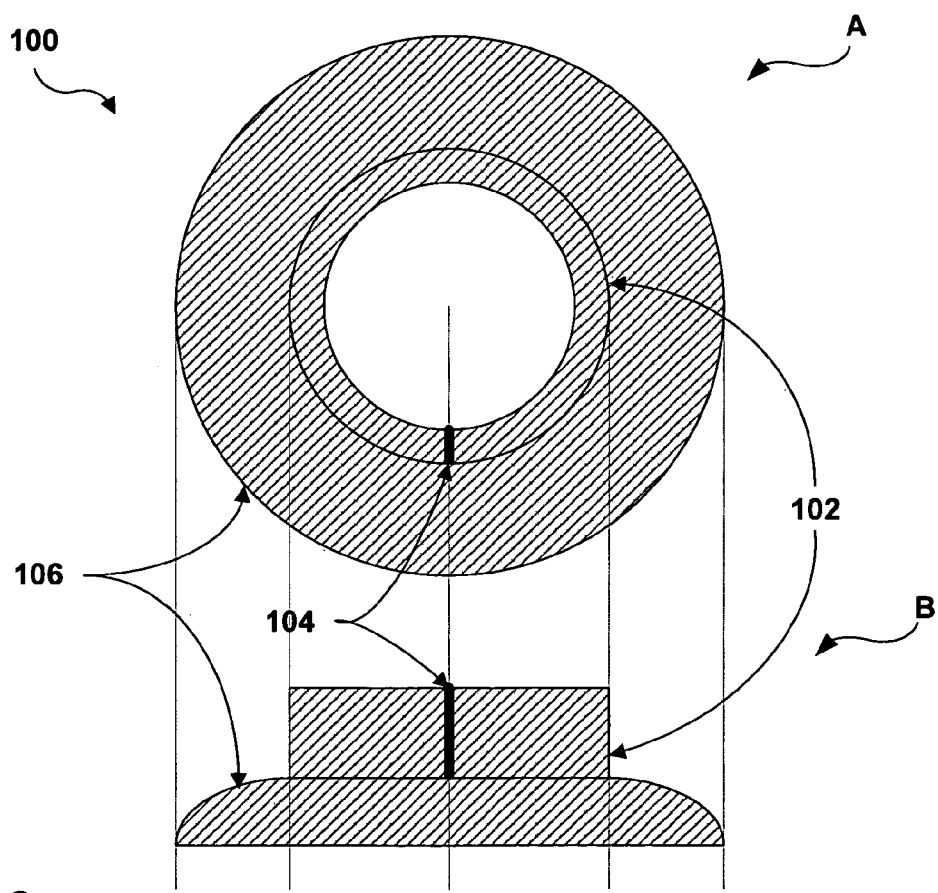
FIG. 8 is a schematic diagram illustrating another exemplary embodiment of a magnetic shield included in a compass-based indicator tool or a locator tool.

FIG. 8 is a schematic diagram illustrating another exemplary embodiment of a magnetic shield 100 included in a compass-based indicator tool conforming to any of indicator tools 10, 30, or 50 or a locator tool conforming to locator tool 70. Magnetic shield 100 includes a cylindrical element 102 formed from a rectangular piece of material, a seam 104 where the opposite ends of the material meet to form cylindrical element 102, and a skirt-like member 106. Skirt-like member 106 is disposed on a sensing side of the compass-based indicator tool, or a locating side of a locator tool, adjacent to cylindrical element 102. A plan view A and a cross-section side view B are shown in FIG. 8; side view B shows the curvature of skirt-like member 106.

Magnetic shield 100 may be used in an indicator tool to block external magnetic fields from influencing a compass during a device setting measurement. Cylindrical element 102 and skirt-like member 106 are made from a material conforming to the material discussed with reference to FIG. 1. Magnetic shield 100 is formed by wrapping a rectangular sheet of the material into substantially cylindrical element 102. The opposite ends of the material meet to create seam 104; seam 104 may be sealed or left open. Cylindrical element 102 may be formed from a thicker piece of Amumetal plate or a thin piece of Amumetal foil.

In either case, the material can be layered to increase the performance of magnetic shield 100. A dielectric adhesive may be used to hold any layers together and to further increase the shielding performance. Skirt-like member 106 is attached adjacent to cylindrical element 102 by welding, or other means to attach two pieces of metal to each other. Skirt-like member 106 may be used to improve the effect of magnetic shield 100 by increasing the area of shielding around the compass.

Skirt-like member 106 may be formed from a thinner piece of Amumetal plate or a piece of Amumetal foil to create a flexible, contoured shape. The flexible skirt-like member 106 may allow magnetic shield 100 to conform to a surface. For example, if the device is a fluid flow control valve implanted beneath a patient's scalp, the flexible skirt-like member 106 may conform to fit the curvature of the patient's head, further reducing the effects of external magnetic fields on the compass.

In one embodiment, magnetic shield 100 is a large cylinder disposed around a compass-based indicator tool housing, as described in reference to FIG. 2 or around a locator tool housing as described in reference to FIG. 4. Prior to taking the device setting measurement, magnetic shield 100 may be slid over the housing and skirt-like member 106 may conform to the surface through which the measurement is being taken. In one specific embodiment, cylindrical element 102 is formed from the 0.102 mm thick metal foil and has a height of approximately 254 mm and a radius of approximately 88.9 mm to fit around the housing, which may be approximately 15.3 mm tall with an outer radius of approximately 35.5 mm. When magnetic shield 100 is slid over the housing, according to one example, the compass is located approximately 114.3 mm from the end of cylindrical element 102 adjacent to the sensing side of the housing.

In another embodiment, cylindrical element 102 is a short cylinder disposed around the compass-based indicator tool housing, as described in reference to FIG. 2 or around the locator tool housing as described in reference to FIG. 4. Again, prior to taking the device setting measurement, magnetic shield 100 may be slid over the housing and skirt-like member 106 may conform to the surface through which the measurement is being taken. As one specific example, cylindrical element 102 is formed from an approximately 0.102 mm thick metal foil and has a height of approximately 44.45 mm and a radius of approximately 69.4 mm to fit around the housing, which may be approximately 15.3 mm tall with an outer radius of approximately 35.5 mm. When magnetic shield 100 is slid over the housing, the compass is flush with the end of cylindrical element 102 adjacent to the sensing side of housing. Magnetic shield 100 will be closer to the compass than in the previously described embodiment, which may increase the shield performance.

In other embodiments, cylindrical element 102 may have a different thickness, height, or radius to fit into a recess formed in the compass-based indicator tool housing around the compass, to fit into a groove formed around the compass in the indicator tool housing, or the like to block external magnetic fields from the compass. Skirt-like member 106 may protrude from the indicator tool and conform to the surface adjacent to the sensing side of the indicator tool.

Figure 9:
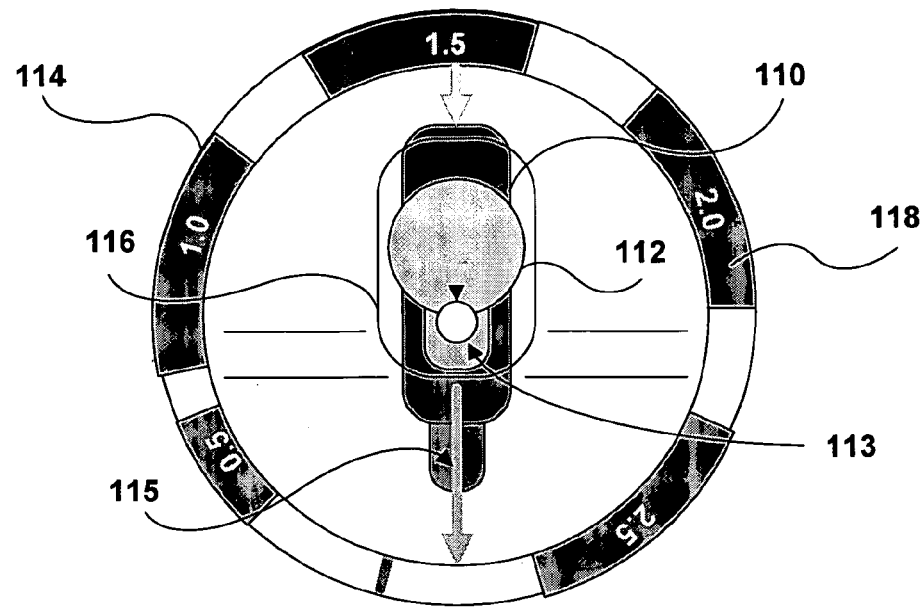
FIGS. 9–11 are schematic diagrams illustrating a system according to an embodiment of the invention.
Figure 10:
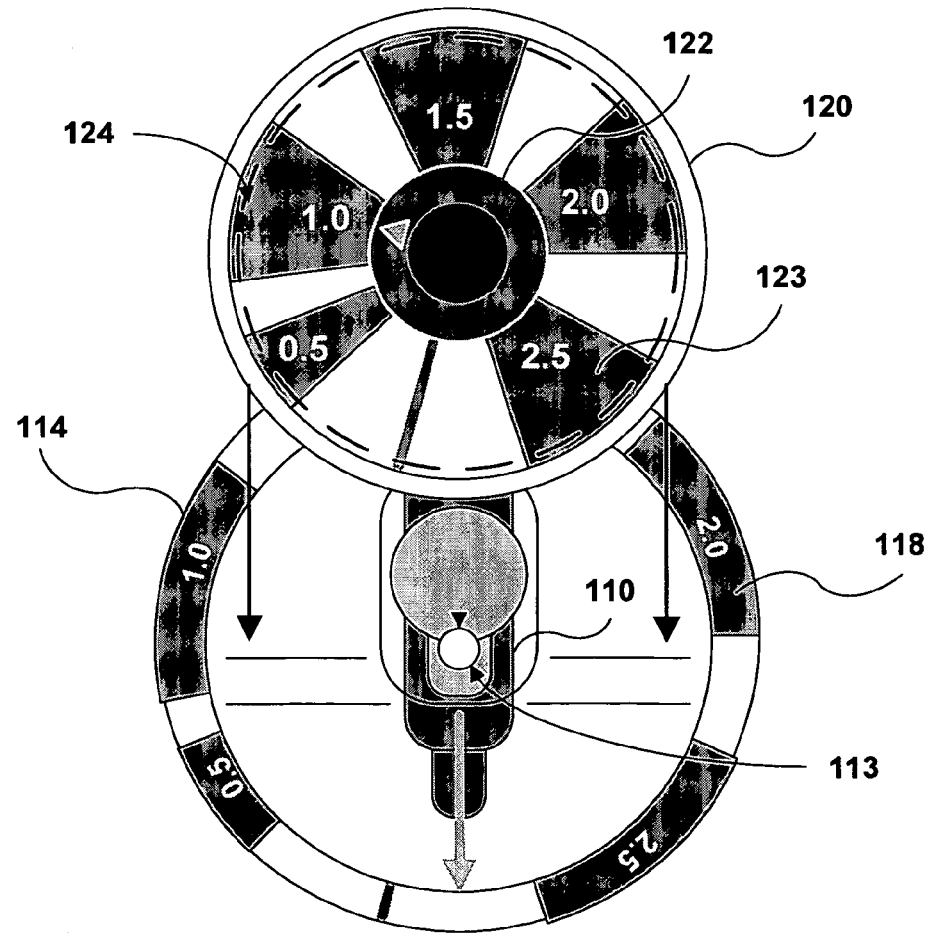
Figure 11:
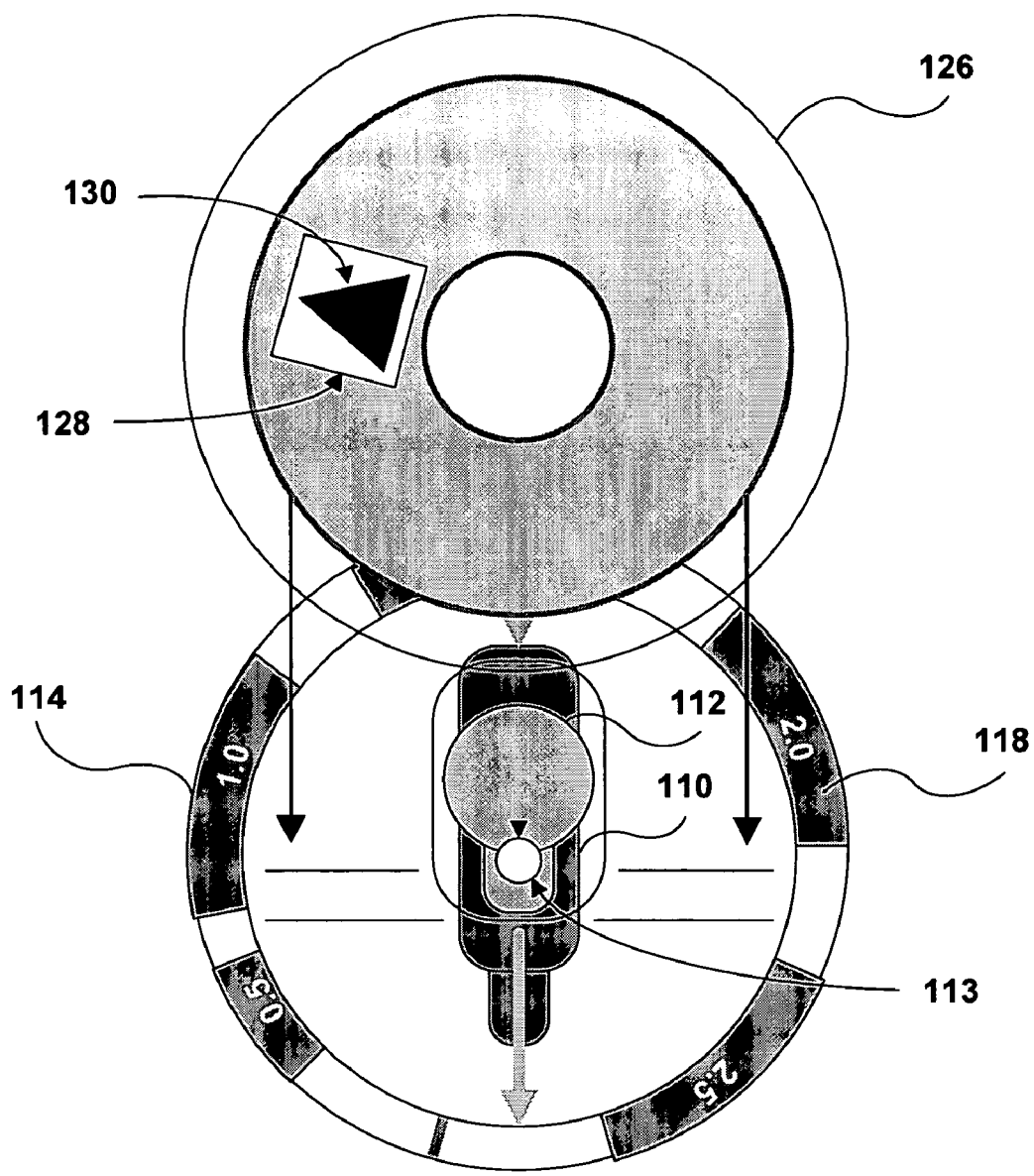

FIGS. 9–11 are schematic diagrams illustrating a system according to an embodiment of the invention. The system includes an implantable medical device 110, a locator tool 114, an indicator tool 120, and an adjustment tool 126. The three tools 114, 120, 126 are used together to determine a setting of the implantable medical device 110 and change the setting in a noninvasive manner.

FIG. 9 is a schematic diagram illustrating a portion of the system involving implantable medical device 110 and locator tool 114. Implantable medical device 110 includes a base 112 and a first magnet 113 embedded within base 112. Locator tool 114 includes an orientation arrow 115, an opening 116, and a device setting index 118.

A device setting of implantable medical device 110 may be changed by rotating base 112. First magnet 113 has a different position for each device setting and creates an internal magnetic field around medical device 110 with a direction related to its position.

In one embodiment, medical device 110 may be a fluid flow control valve used to control cerebral spinal fluid (CSF) pressure in a patient's brain. The valve is implanted on the patient's skull beneath the scalp. Medical device 110 is located by palpating the scalp. Locator tool 114 is then properly fit over medical device 110 by aligning orientation arrow 115 with the orientation of medical device 110, as in FIG. 9.

FIG. 10 is a schematic diagram illustrating another portion of the system involving implantable medical device 110, locator tool 114, and compass-based indicator tool 120. Indicator tool 120 includes a compass 122, a device setting index 123, and a magnetic shield 124. As shown in FIG. 10, indicator tool 120 couples to locator tool 114. Indicator tool 120 aligns with the orientation of both locator tool 114 and implantable medical device 110 by matching device setting index 123 with the locator tool device setting index 118.

Compass 122 may interact with first magnet 113 on medical device 110 when indicator tool 120 is coupled to locator tool 114. Compass 122 may indicate the device setting by aligning with the internal magnetic field created by first magnet 113, and pointing to a region on device setting index 123 and 118. External magnetic fields may cause compass 122 to deflect from the internal magnetic field and indicate an incorrect value on device setting index 123. Magnetic shield 124 blocks at least a portion of the external magnetic fields to allow compass 122 to indicate an accurate device setting measurement.

FIG. 11 is a block diagram illustrating another portion of the system involving implantable medical device 110, locator tool 114, and adjustment tool 126. Adjustment tool 126 includes a second magnet 128 and a pointer 130. As shown in FIG. 11, adjustment tool 126 couples to locator tool 114, and second magnet 128 couples to first magnet 113. Adjustment tool 126 properly aligns with implantable medical device 110 and locator tool 114 by matching pointer 130 to the device setting value indicated on device setting index 118 by compass 122, as described in reference to FIG. 10.

If first magnet 113 and second magnet 128 are coupled, then rotating adjustment tool 126 moves base 112 as well. In this way, adjustment tool 126 may change the device setting of implantable medical device 110 and indicator tool 120 may check the device setting value without surgery to remove medical device 110.

Figure 12:
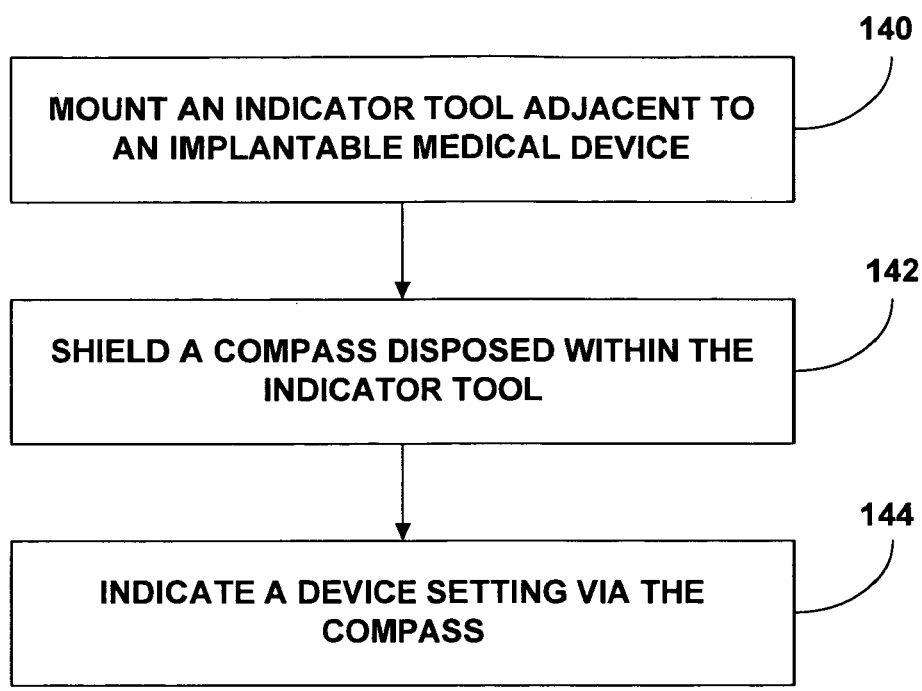
FIG. 12 is a flow diagram illustrating a method for using a compass-based indicator tool.

FIG. 12 is a flow diagram illustrating a method for using a compass-based indicator tool 120. Indicator tool 120 is mounted adjacent to an implantable medical device 110 (140). A compass 122 disposed within indicator tool 120 interacts with a first magnet 113 embedded in medical device 110. Compass 122 aligns with the internal magnetic field around medical device 110 produced by first magnet 113. External magnetic fields may influence compass 122 to deflect from the internal magnetic field. A magnetic shield 124 is disposed within or around indicator tool 120 and at least partially surrounds compass 122 (142). Magnetic shield 124 blocks at least a portion of external magnetic fields from influencing compass 122. Compass 122 may then indicate an accurate device setting value (144) by aligning with the internal magnetic field and pointing to a region on a device setting index 123 disposed on indicator tool 120.

Figure 13:
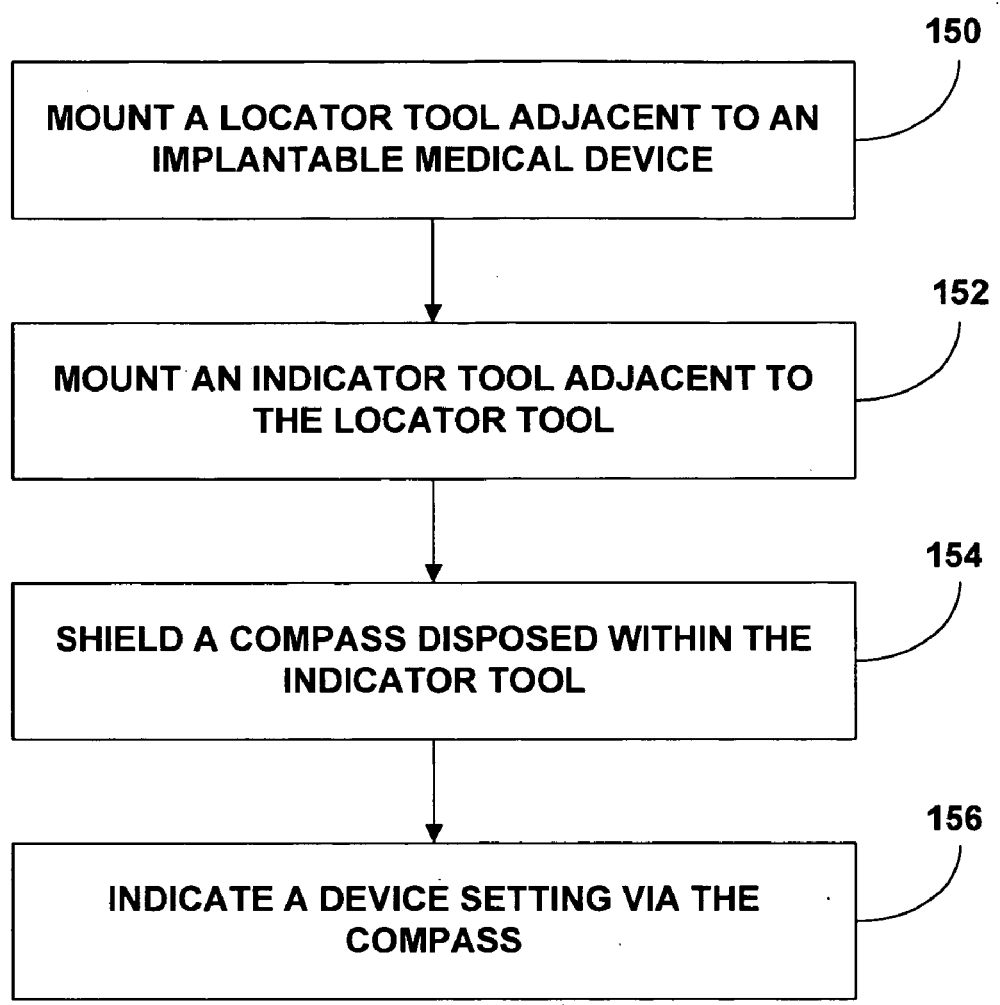
FIG. 13 is a flow diagram illustrating a method for using a compass-based indicator tool with a locator tool.

FIG. 13 is a flow diagram illustrating a method for using a compass-based indicator tool 120 with a locator tool 114. Locator tool 114 is mounted adjacent to an implantable medical device 110 (150). Locator tool 114 aligns with the orientation of implantable medical device 110 by fitting an opening 116 over the device 110. Indicator tool 120 is mounted adjacent to the locator tool (152). The indicator tool 120 aligns with implantable medical device 110 and locator tool 114 by matching an indicator tool device setting index 123 to a locator tool device setting index 118.

A compass 122 disposed within indicator tool 120 interacts with a first magnet 113 on medical device 110. Compass 122 aligns with the internal magnetic field around medical device 110 produced by first magnet 113. External magnetic fields may influence compass 122 to deflect from the internal magnetic field. A magnetic shield 124 is disposed within or around indicator tool 120 or around locator tool 114 and at least partially surrounds compass 122 (154). Magnetic shield 124 at least partially blocks the external magnetic fields from influencing compass 122. Compass 122 may then indicate an accurate device setting value (156) by aligning with the internal magnetic field and pointing to a region on device setting index 118 and 123 disposed on locator 114 and indicator tool 120.

Figure 14:
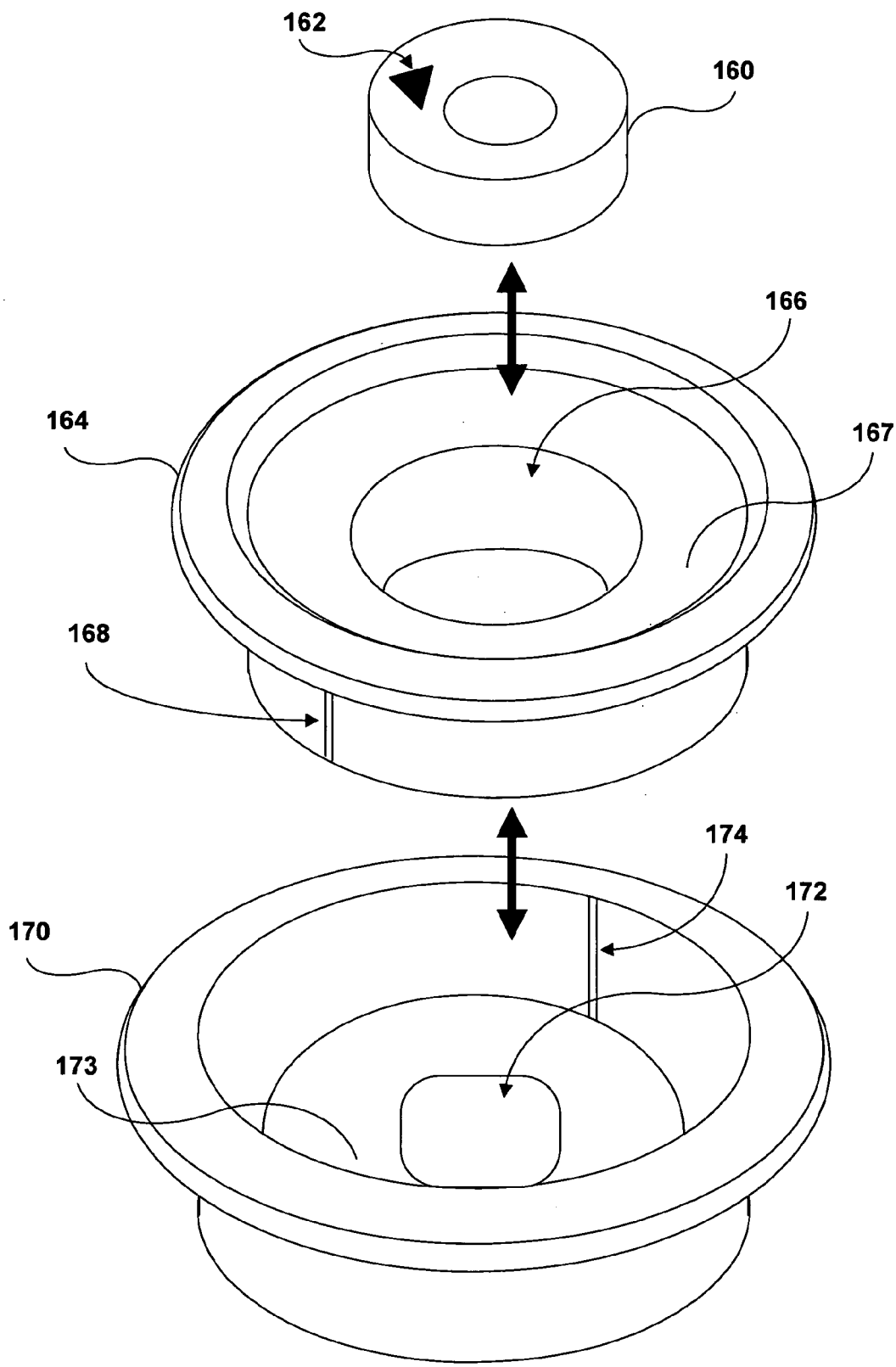
FIG. 14 is an exploded schematic diagram illustrating a compass, an indicator tool, and a locator tool.

FIG. 14 is an exploded schematic diagram illustrating a compass 160, an indicator tool 164, and a locator tool 168. Compass 160 includes a compass needle 162. Indicator tool 164 includes an opening 166 in a housing 167 and conformal shapes 168. Locator tool 170 includes an opening 172 in a housing 173 and conformal shapes 174.

As an example, a fluid flow control valve may be subcutaneously implanted on a patient's skull. A magnet is embedded on the valve and has a position relative to a valve setting. The valve has an orientation which can be determined by palpating the valve through the patient's skin. The valve is then fit into opening 172 in housing 173 of locator tool 170 according to the orientation.

The valve setting may be determined through magnetic coupling between the valve magnet and compass 160. Compass needle 162 interacts with a magnetic field created by the magnet to indicate the valve setting value. In order for the indicated value to be accurate, compass 160 is be placed as close to the magnet as possible to maintain a strong interaction. Compass 160 is permanently fixed into opening 166 in housing 167 of indicator tool 164.

Indicator tool 164 couples to housing 173 of locator tool 170. Conformal shapes 168 and 174 connect to align indicator tool 164 with locator tool 170 and with the orientation of the valve. Therefore, compass needle 162 may interact with the valve magnet and indicate an accurate value of the valve setting.

The preceding specific embodiments are illustrative of the practice of the invention. It is to be understood, therefore, that other expedients known to those skilled in the art or disclosed herein may be employed without departing from the invention or the scope of the claims. For example, a magnetic shield for a compass-based indicator tool has been described that is disposed within a recess in a housing of the compass-based indicator tool.

The magnetic shield surrounds a compass disposed in the housing and blocks external magnetic fields from influencing the compass reading. The magnetic shield is also small enough to remain invisible to a user of the tool. Another magnetic shield was described that fit over the entire housing. The magnetic shield of that embodiment is highly visible to the user, but may be able to block more external magnetic fields due to its large area of coverage and provide for a more accurate reading from the compass.

In the claims, any means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

What is claimed is:

1. A system comprising:
   an implantable fluid flow control valve for cranial implantation to control flow of cerebral spinal fluid within a patient;
   a first magnet carried by the fluid flow control valve to indicate a valve setting;
   a compass that interacts with the first magnet to determine the valve setting;
   a magnetic shield surrounding at least a portion of the compass to reduce effects of an earth magnetic field on the compass; and
   an adjustment tool having a second magnet that interacts with the first magnet to change the valve setting.

2. A method comprising:
   applying a compass to determine a valve setting of an implantable cerebral spinal fluid flow control valve implanted in a cranium of a patient, wherein the compass interacts with a first magnet carried by the fluid flow control valve to determine the valve setting;
   applying a second magnet that interacts with the first magnet to change the valve setting; and
   shielding the compass with a magnetic shield surrounding at least a portion of the compass to reduce effects of an earth magnetic field on the compass.

3. A shield for a compass-based indicator tool used to determine a valve setting of a cranially implanted cerebral spinal fluid valve, the shield comprsiing:
   a substantially annular shaped frame sized to fit around a circumference of a compass within a compass-based indicator tool; and
   multiple layers of a magnetic shielding materal wrapped around the frame.

* * * * *

UNITED STATES PATENT AND TRADEMARK OFFICE
CERTIFICATE OF CORRECTION

| | | |
|---|---|---|
| PATENT NO. | : 6,951,059 B2 | Page 1 of 1 |
| APPLICATION NO. | : 11/042400 | |
| DATED | : October 4, 2005 | |
| INVENTOR(S) | : Ari Moskowitz and Marc Stepkowski | |

It is certified that error appears in the above-identified patent and that said Letters Patent is hereby corrected as shown below:

Column 14, line 56, "shield comprsiing" should be --shield comprising--.

Signed and Sealed this

Twenty-sixth Day of June, 2007

JON W. DUDAS
*Director of the United States Patent and Trademark Office*